United States Patent [19]

Hara

[11] Patent Number: 5,344,398

[45] Date of Patent: Sep. 6, 1994

[54] HEATED BALLOON CATHETER

[75] Inventor: Shinji Hara, Tokyo, Japan

[73] Assignee: Japan Crescent, Inc., Japan

[21] Appl. No.: 19,664

[22] Filed: Feb. 19, 1993

Related U.S. Application Data

[63] Continuation-in-part of Ser. No. 984,490, Dec. 2, 1992, abandoned.

[30] Foreign Application Priority Data

| Feb. 25, 1992 | [JP] | Japan | 4-38128 |
| Apr. 22, 1992 | [JP] | Japan | 4-103230 |
| Apr. 22, 1992 | [JP] | Japan | 4-103231 |

[51] Int. Cl.$^5$ ............................................. A61M 29/00
[52] U.S. Cl. .................................... 604/96; 604/21; 606/192
[58] Field of Search ............... 128/400, 401, 658; 604/20, 21, 30, 31, 67, 113, 102, 103, 96; 606/28, 174, 27, 172, 29, 31

[56] References Cited

U.S. PATENT DOCUMENTS

| 4,512,762 | 4/1985 | Spears | 604/21 |
| 4,773,899 | 9/1988 | Spears | 604/20 |
| 4,799,479 | 1/1989 | Spears . | |
| 4,878,492 | 11/1989 | Sinofsky et al. . | |
| 4,955,377 | 9/1990 | Lennox et al. | 128/401 |
| 5,019,075 | 5/1991 | Spears et al. | 606/7 |
| 5,084,060 | 1/1992 | Freund et al. | 606/192 |
| 5,092,841 | 3/1992 | Spears | 604/96 |
| 5,191,883 | 3/1993 | Lennox et al. | 128/401 |
| 5,211,631 | 5/1993 | Sheaff | 604/113 |
| 5,236,413 | 8/1993 | Feiring | 604/21 |
| 5,246,438 | 9/1993 | Langberg | 606/33 |

Primary Examiner—C. Fred Rosenbaum
Assistant Examiner—V. Alexander
Attorney, Agent, or Firm—Quarles & Brady

[57] ABSTRACT

A heated balloon catheter for treatment of constricted zones of body fluid passages by applying heat and pressure to the constricted zone. The heat is generated by transmitting, to an antenna within a balloon carried by the catheter, radio frequency energy of about 13.56 MHz. Measuring the temperature of the balloon inflating fluid and controlling the temperature of the balloon inflating fluid to prevent overheating of the zone being treated and providing an alarm if the balloon leaks or bursts.

15 Claims, 2 Drawing Sheets

HEATED BALLOON CATHETER

CROSS-REFERENCE TO RELATED INVENTION

This application is a continuation-in-part of my application titled "Heated Balloon Catheter—Case I," Shinji Hara, filed in the U.S. Patent and Trademark Office on Dec. 2, 1992, and assigned Ser. No. 07/984,490.

FIELD OF THE INVENTION

This invention relates to a heated balloon catheter having utility in a number of fields for treatment of humans, for example, elimination or reducing atherosclerosis; heart valve stenosis; dilation of the prostate, esophagus, and hepatic duct, etc.

The invention will be specifically described in respect to percutaneous translumenal coronary angioplasty (PTCA).

BACKGROUND OF THE INVENTION

Hot balloon catheters are known in the art for PTCA treatment wherein cardiac catheterization is carried out by directing an inflatable balloon in a coronary artery in the region of a coronary narrowing, and U.S. patents disclosing such treatment are J. R. Spears Pat. Nos. 4,512,762; 4,773,899; 4,799,479; 5,019,075 and 5,092,841; and Sinofsky et al. 4,878,492.

SUMMARY OF THE INVENTION

The invention can be generally defined as including a tube having lumens therein, an inflatable thin-walled balloon secured to the distal end of the tube, and means for directing an inflating fluid to and from the interior of the balloon via one or more lumens of the tube. Within the balloon are housed a radio frequency (R.F.), in the order of 1 MHz to 28 MHz, heater electrode; a thermocouple; and a guide wire for positioning the assembly adjacent the coronary narrowing. At the frequency region of 1 MHz to 28 MHz, the R.F. may behave like a DC current over a copper wire conductor. Above this frequency range, R.F. and VHF (100 MHz, and above), a simple copper wire conductor cannot be used, and special conductors, such as coaxial cables, must be used. This invention includes the above features, plus means for preventing overheating of the intima at the zone of the stenosis and alarm and shut-off means to warn of balloon breakage or leakage and to prevent excessive fluid flow into the blood stream.

OBJECTIVES AND RELATED EXPERIMENTAL FINDINGS

Through experiences in experimental human cases with applicant's heated balloon catheter and also from scientific reports and verbal communication with competitive devices, it has now become clear that HB PTCA (Thermal Angioplasty) may cause very high (as high as 80%) early re-stenosis (within 3 months after the operation).

The above findings are reproducible when higher heat (above 80° C.) in the balloon is used; while, if the balloon temperature is kept below 60° C., such high restenosis does not occur.

Between 60–80° C., there is a temperature where acute protein denaturation occurs. The exact temperature varies depending upon the protein to be heated.

A temperature of about 63° C. is used for serialization of milk, for example, to kill all bacteria in the milk for preservation.

When touching an object over 63° C., the skin shows immediate white burn. If such burn would occur in a coronary artery, it would cause discontinuity in the vessel and cause clotting.

Below this temperature, human protein can tolerate heat for as much as one to thirty minutes before permanent burn, known as low-temperature burn, occurs.

In Chinese medicine, this heat (63° C. and below) effect is used to stimulate the human body, while not leaving a skin burn (typically using hot wax).

Control of the temperature below 63° C. can be achieved by controlling RF power to heat a balloon, but, sometimes, it has been found that there are still high temperature burns due to local hot-spot formation.

In order to avoid this problem, the applicant is providing a device in which coolant is circulated in the balloon, thereby reducing the temperature of the balloon and the contacting intima of the vessel to a temperature below protein denaturation temperature.

BRIEF DESCRIPTION OF THE DRAWINGS

The invention will be more particularly described in reference to the accompanying drawings wherein.

DETAILED DESCRIPTION OF THE INVENTION

Figure 1:
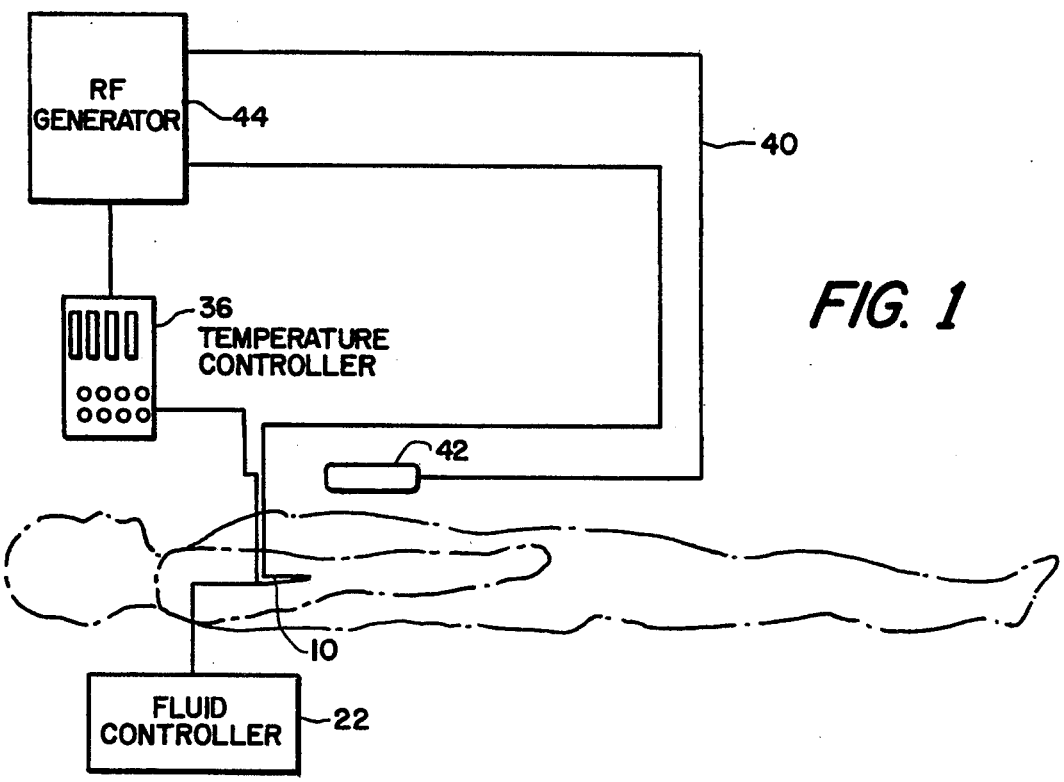
FIG. 1 is a diagrammatic view of a system for PTCA treatment employing a heated balloon catheter.
Figure 2:
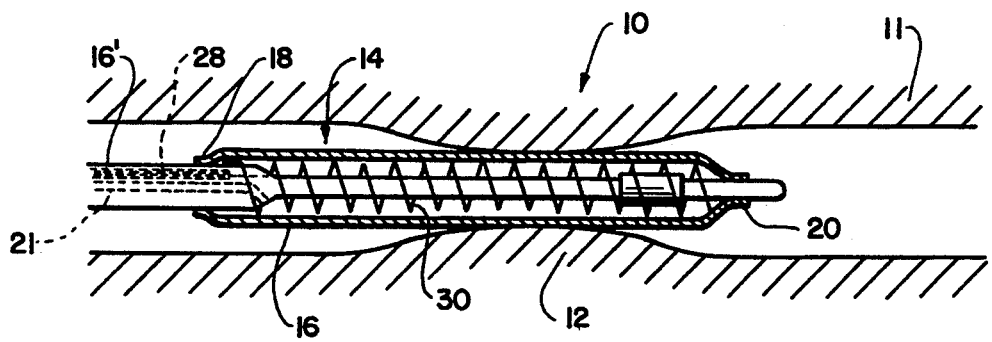
FIG. 2 is an enlarged view of the balloon end of a catheter constructed in accordance with the present invention positioned in active relationship to a stenosis with the balloon deflated.

Referring to FIGS. 1 and 2 of the drawings, 10 generally designates, in schematic form, the distal end of a thermal PTCA balloon catheter. Reference number is an artery having a region of stenosis designated 12. Into the region is inserted the distal end of the balloon catheter, generally designated 14, which includes a thin-walled balloon 16.

In fabricating the balloon, the thickness of the balloon membrane is important for efficient transfer of R.F. energy across the balloon membrane and other forms of heat transfer; thus, the thinner the membrane, the better the operation of the catheter.

In one form of heat transfer, the energy transfer is based upon capacitive effect; the thinner the membrane, the better the energy transfer.

Mechanical strength is not particularly important with applicant's PTCA catheter, since applicant can dilate the stenosis at much lower pressure, such as 2–6 atm, while conventional balloons without heat now dilate at 10–15 atms. This is one of the reasons that the hot balloon PTCA is very attractive for clinical doctors, as high pressure is more dangerous if a balloon ruptures.

Typically, the membrane should be less than 20 microns, while sometimes up to 100 microns are used for a balloon where a stronger wall is necessary. The balloon is usually constructed of polyethylene terephthalate or polyethylene, while other materials, such as urethane, may be employed.

The catheter according to the present invention is preferably designed such that the outside diameter of the balloon can be increased from about 1.5 mm to 10.0 mm when the balloon is inflated. Fluids which may be used for inflating the balloon include an angiographic reagent or a solution of about 0.9% sodium chloride and water.

The balloon is sealed at its ends 18 and 20 to a, preferably, three-lumen catheter tube 16'. The catheter tube 16', in the illustrated form of the invention, has three lumens, as disclosed in my application Ser. No. 07/984,490 and has one lumen 21 about 400 microns in diameter for the feed-in-and-out of a coolant fluid via controller 22. Lumen 21, for coolant, also is used for pressurizing the balloon.

Figure 5:
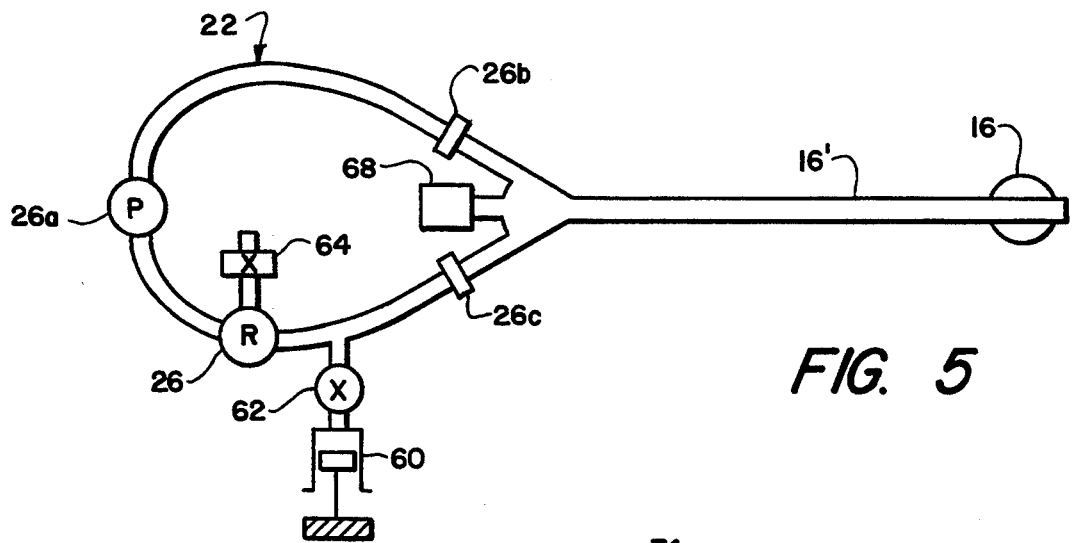
FIG. 5 is a diagrammatic view of a system for controlled inflation of the heated balloon of the balloon catheter.

In FIG. 5, item 22, there is illustrated a source of fluid 26 and a pressurizing pump 26a, having valve means 26b and 26c for control of the amount and direction of fluid flow.

Figure 3:
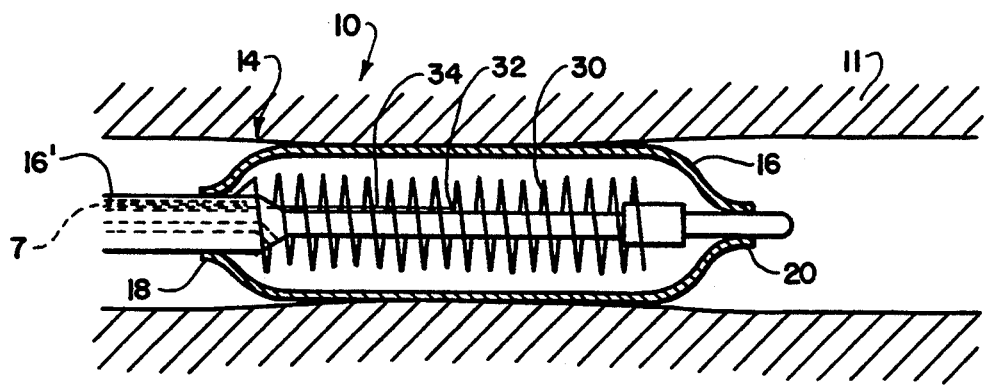
FIG. 3 is a view like FIG. 2 with the heated balloon in the expanded position.

Again, referring to both FIGS. 1-3, the third lumen 28 houses the stainless steel coil 30, having an internal diameter of about 500 microns. The wire diameter of the coil may be 10 to 100 microns. The length of the stainless steel coil 30 has, in a preferred form of the invention, a length of approximately 150 centimeters. Another element at the distal end of the catheter is a thermocouple 32, having connection to the stainless steel coil 30, and a copper wire 34.

In a preferred form of the invention, the R.F. generator should be crystall-controlled oscillator.

In a preferred form of the invention, the R.F. generator should be a crystall-controlled oscillator.

The thermocouple is, as disclosed in application Ser. No. 07/984,490, connected via said stainless steel coil 30 and copper wire 34 to an external temperature controller 36 to be further discussed hereinafter. Referring to FIG. 3, the present invention constructs an internal electrode in a portion of the stainless steel coil 30 adjacent to the thermocouple 32 within the balloon 16. The internal electrode is an antenna provided within the balloon 16. The other electrode 42 is preferably in contact with a patient and can be positioned as shown in FIG. 1. Said internal electrode is, as disclosed in application Ser. No. 07/984,490, connected via said copper wire 34 to an RF generator 44 located externally of the patient, in order to receive an RF energy therefrom. Said other external electrode is connected to said RF generator 44 via conductor 40, which transmits 13.56 MHz radio frequency.

In a preferred form of the invention, the R.F. generator should be a crystall-controlled oscillator.

Coupled with the system, there may be a filtering network, in order to properly measure the temperature within the heated balloon, as disclosed in my said companion application, Ser. No. 07/984,490.

In order to measure temperature where R.F. energy is used to heat the tissue around the balloon, one must eliminate the R.F. signal to the temperature controller 36. A good rejection filter in the thermometer is necessary. An active rejection filter should have −100 db rejection at 13.56 MHz. Since active filters can filter out (reject) "noise" at specific frequencies, it is important that the noise source, that is the R.F. energy, for heating the balloon be as pure as possible, which in this case is 13.56 MHz.

It has been discovered that even with control of the cooling fluid temperature and flow rate, it is difficult to measure the temperature 3 to 5 mm within the intima. To keep this zone from overheating, the temperature controller is provided with stored temperature distribution data.

Late re-stenosis is one of the most serious problems of PTCA procedures. It has been found that the rate of re-stenosis is between at least about 20–40% over a five-year period. It is applicant's considered opinion that the re-stenosis is probably caused, in part, by irregular surfaces at the intima of the vessel dilated, since the blood vessel clots when there is excess heating. During tests performed, where the stenosis was treated at a temperature of 80° C., within three months it was found that early re-stenosis of dilated vessels was as high as 80%. It has now been discovered that by carefully controlling the temperature of hot balloon procedures so that the intima of blood vessels is maintained not greater than 42° C., the chances of re-stenosis are materially reduced. In order to control heating to below 42° C. using the hot balloon technique, heating of the fluid at temperatures of 39-62° will permit carrying out the procedures with minimal permanent damage to the tissue, whereas temperatures above 42° C. may cause some permanent damage to the tissue and, thus, increase the chances of re-stenosis.

Figure 4:
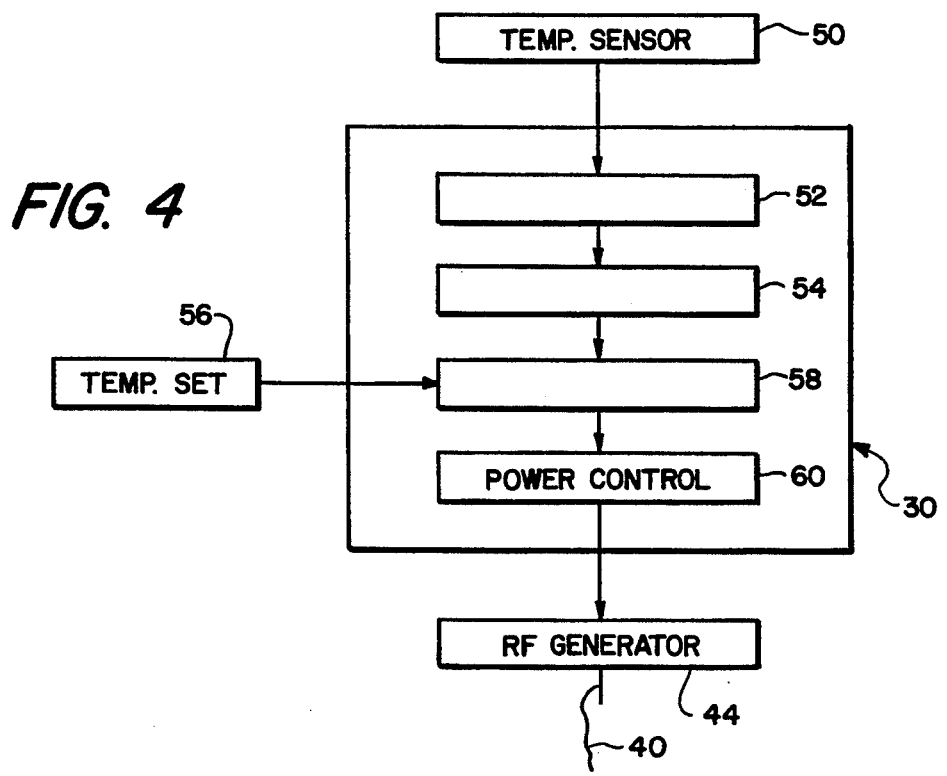
FIG. 4 is an expanded view of the temperature and power controller useful with the present invention.

Referencing FIG. 4 of the drawing, there is illustrated, in block diagram form, temperature sensing and control apparatus 36, which has been proven to maintain stenosis heating at 42° C. and below. In FIG. 4, the controller includes a temperature sensor 50 for sensing the temperature of the fluid employed in inflating the balloon 16. The sensed temperature is directed to a detector 52 and a calculator 54. Means 56 designates conventional means whereby the desired temperature may be set, and the sensed temperature is directed along with the calculated fluid temperature to a comparator designated 58. The output from the comparator is directed to a conventional power control module 60, which directs its control function to the R.F. generator 44 for transmitting the R F heating voltage to the internal electrode within the balloon 16 via copper wire 34, whereby the zone surrounding the balloon 16 and the fluid contained in the balloon 16 are capable of being heated according to the capacitive heating principal.

Figure 6:
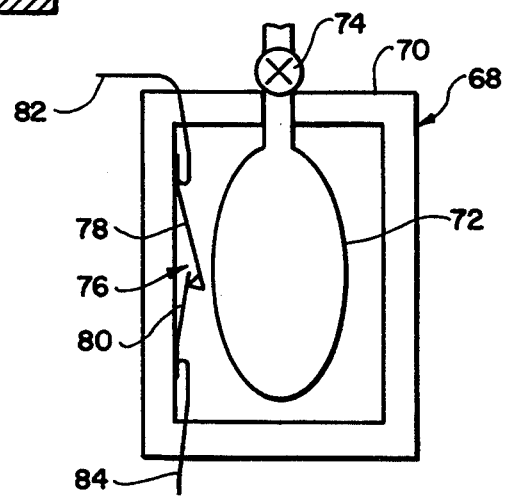
FIG. 6 is a diagrammatic view of an alarm for detecting leakage or breakage of the balloon of the heated balloon catheter.

Another problem inherent in the use of heated balloon catheters is the possibility of fluid leakage from the balloon or balloon rupture. In the event of leakage or balloon rupture, it is necessary that the physician be immediately apprised so that the pump 26a can be deactivated or reversed to prevent further fluid from flowing into the vein or artery and/or to remove fluid from the leaking or ruptured balloon, all by means of the automatic shut-off mechanism hereafter disclosed Referring now to FIGS. 5 and 6, a system for directing fluid to the balloon of the balloon catheter includes a fluid reservoir 26, a pump 26a, and the previously mentioned flow control valves 26b and 26c. In order to control inflation, the system includes a positive displacement pump, such as illustrated at 60, and a valve 62. The fluid reservoir 26 preferably has a reservoir volume of approximately 3CC to limit the fluid volume which may be injected into the body upon balloon failure.

In operation, the pressure-fluid lines in the catheter 16' and balloon 16 are filled with the inflating fluids, such as angiographic reagent, via the pump 26a and flow-control valves 26b and c. The fluid is directed from the reservoir 26, and air being expelled from the conduits and balloon is bled from the reservoir via flow-control valve 64. At this stage, the positive acting pump 60 directs the desired pressure into the catheter 16' to properly inflate the balloon 16.

Another feature of the present invention is an alarm system for detecting balloon leakage or rupture consisting of means illustrated at 68 comprising a housing 70 into which is mounted a small sensor balloon 72, maintained via valve 74 at a pressure equivalent to that of balloon 16. The housing 70 mounts a conventional switch, generally designated 76, having a movable contact member 78 which engages a surface of the balloon 72 and a fixed contact 80 connected via conductors 82 and 84 to a light signal or audible alarm, or both. Any leakage or bursting of the balloon 16 will cause the balloon 72 to deflate, whereby the movable electrical contact element 78 moves out of electrical contact with fixed electrical terminal 80 to break the circuit and the visual and/or audible alarms are actuated. The physician then disconnects power to the pumps 26a and 66 and the controller 36.

Since this is the closed circuitry, the pressure and the volume of coolant can be immediately decreased when the balloon ruptures. Thus, this embodiment of the present invention provides an automatic shut-off of the pressure and feeding of the coolant to keep the coolant injected into the human body to a minimum.

Another safety feature in applicant's inflation circuitry is the use of high-pressure resistant, braided wiring 70 for all high-pressure components of the unit illustrated in FIG. 5.

I claim:

1. A heated balloon catheter for treatment of constricted zones of body fluid passages by applying heat and pressure to the constricted area comprising:
    a catheter and a balloon secured to the distal end of the catheter, said balloon defining an internal volume communicating with at least one longitudinal passage in the catheter,
    means for directing pressurized fluid to and from the internal volume of said balloon through said at least one longitudinal passage,
    heat sensing means for the fluid in the balloon, electrical conductors connecting the heat sensing means with an external temperature controller.
    an internal electrode within the balloon,
    an external electrode outside the balloon, said external electrode being in contact with a patient body,
    an R.F. generator external to the catheter, and electrical conductors connecting the R.F. generator to the internal and external electrodes to provide capacitive heating of the tissue surrounding said balloon, and
    control means for maintaining a temperature in the zone of constriction not greater than a protein denaturation temperature.

2. The heated balloon catheter, as defined in claim 1, wherein the temperature is not greater than 42° C.

3. The heated balloon catheter, as defined in claim 1, wherein the temperature is maintained between 39°–62° C.

4. The heated balloon catheter, as defined in claim 1, wherein the energy for heating the fluid contained in the balloon and the zone surrounding the balloon is radio frequency in the order of 13.56 MHz.

5. The catheter, as defined in claim 4, wherein the outside diameter of the balloon can be increased from about 1.5 mm to 10.0 mm upon inflation.

6. The catheter, as defined in claim 5, wherein the balloon is inflated with a solution of about 0.9% sodium chloride and water.

7. The invention defined in claim 5, wherein the balloon is inflated with an angiographic reagent.

8. The invention defined in claim 5; wherein the inflating fluid is heated to about 39–62° C.

9. The invention, as defined in claim 4, further comprising a temperature sensing and control apparatus wherein a desired fluid temperature is compared with a measured temperature of the fluid, and the power output of the R.F. generator is increased or decreased by said temperature sensing and control apparatus based upon a comparison between the desired and measured temperatures.

10. The invention, as defined in claim 9, wherein the temperature sensing and control apparatus contains a microprocessor which receives data relating to the R.F. power output, the desired fluid temperature, and the measured temperature and, with the use of stored heat distribution data, controls the timing interval of the R.F. energy on/off cycle.

11. The invention defined in claim 1, further including an alarm activated by balloon breakage or balloon leakage.

12. The invention defined in claim 11, further including a cooling fluid circulating pump and means for automatically stopping said pump if the balloon ruptures.

13. The invention, as defined in claim 11, further comprising a sensor housing, a sensor balloon in fluid communication with said catheter balloon, and a pressure-sensitive balloon switch, said sensor balloon and said balloon switch being mounted within said housing such that, upon leakage of fluid from said catheter balloon, said sensor balloon will deflate thereby actuating the pressure sensitive switch.

14. The invention defined in claim 13, wherein a wall of the sensor balloon actuates and deactivates said pressure-sensitive switch by engaging a movable contact member on said pressure sensitive switch.

15. The invention, as defined in claim 11, further including a small reservoir and high-pressure pump, said high pressure pump being used to circulate coolant to the balloon and to pressurize the balloon and said longitudinal passage, said small reservoir for the circulating coolant, said reservoir having a volume in the order of 3 cc to thereby limit the fluid volume which may be injected into the body upon balloon failure.

* * * * *